(12) United States Patent
Rithener et al.

(10) Patent No.: US 10,561,267 B2
(45) Date of Patent: *Feb. 18, 2020

(54) INTER-OPERABLE CAPSULE DISPENSING UNIT AND BEVERAGE PREPARATION MACHINE

(71) Applicant: Nestec S. A., Vevey (CH)

(72) Inventors: Blaise Rithener, La Tour-de-Peilz (CH); Antoine Cornet, Epesses (CH)

(73) Assignee: Societe des Produits Nestle S.A., Vevey (CH)

( * ) Notice: Subject to any disclaimer, the term of this patent is extended or adjusted under 35 U.S.C. 154(b) by 145 days.

This patent is subject to a terminal disclaimer.

(21) Appl. No.: 15/502,346

(22) PCT Filed: Aug. 20, 2015

(86) PCT No.: PCT/EP2015/069141
§ 371 (c)(1),
(2) Date: Feb. 7, 2017

(87) PCT Pub. No.: WO2016/026929
PCT Pub. Date: Feb. 25, 2016

(65) Prior Publication Data
US 2017/0224151 A1    Aug. 10, 2017

(30) Foreign Application Priority Data
Aug. 21, 2014    (EP) .................................... 14181722

(51) Int. Cl.
*A47J 31/36*    (2006.01)
*G05B 15/02*    (2006.01)
*G06F 19/00*    (2018.01)

(52) U.S. Cl.
CPC .......... *A47J 31/3642* (2013.01); *G05B 15/02* (2013.01); *G06F 19/3462* (2013.01)

(58) Field of Classification Search
CPC .. B65D 85/8043; A47J 31/3642; G06F 19/00; G06F 19/3462; G05B 15/02
(Continued)

(56) References Cited

U.S. PATENT DOCUMENTS 5,350,082 A * 9/1994 Kiriakides, Jr. ...... G07F 13/065
221/1
7,743,622 B2 * 6/2010 Fischer .................. F25C 5/046
62/344

(Continued)

FOREIGN PATENT DOCUMENTS

WO    2005104911 A1    11/2005
WO    2016026928 A1    2/2016

OTHER PUBLICATIONS

International Search Report, dated Oct. 2, 2015, in PCT/EP2015/069141, filed Aug. 20, 2015.

(Continued)

*Primary Examiner* — Dana Ross
*Assistant Examiner* — Kuangyue Chen
(74) *Attorney, Agent, or Firm* — K&L Gates LLP

(57) ABSTRACT

A beverage preparation system is disclosed that includes a capsule dispenser and a beverage preparation machine that are operatively linked by a control system. Also disclosed is a method of preparing a beverage using the beverage preparation system. In addition, a capsule dispenser, a beverage preparation machine, a computer program for a processing unit of a control system, and a non-transitory computer readable medium comprising the computer program are also disclosed.

12 Claims, 5 Drawing Sheets

(58) Field of Classification Search
USPC .......................................................... 99/295
See application file for complete search history.

(56) References Cited

U.S. PATENT DOCUMENTS

| | | | | |
|---|---|---|---|---|
| 2004/0112222 | A1* | 6/2004 | Fischer | ............... A47J 31/3628 |
| | | | | 99/279 |
| 2004/0194629 | A1* | 10/2004 | Jones | .................... A47J 31/402 |
| | | | | 99/275 |
| 2005/0015348 | A1 | 1/2005 | Knepler | |
| 2007/0246478 | A1* | 10/2007 | Jarisch | ...................... A47F 1/10 |
| | | | | 221/123 |
| 2011/0082595 | A1* | 4/2011 | Mehus | ..................... B67D 7/02 |
| | | | | 700/283 |
| 2015/0125586 | A1* | 5/2015 | Ergican | ................. A47J 31/407 |
| | | | | 426/590 |

OTHER PUBLICATIONS

Written Opinion of the International Searching Authority, dated Oct. 2, 2015, in PCT/EP2015/069141, filed Aug. 20, 2015.
International Search Report, dated Oct. 2, 2015, in PCT/EP2015/069139, filed Aug. 20, 2015.
Written Opinion of the International Searching Authority, dated Oct. 2, 2015, in PCT/EP2015/069139, filed Aug. 20, 2015.
U.S. Appl. No. 15/502,663; Rithener, et al.; Office Action dated Feb. 7, 2019; filed Feb. 8, 2017.

* cited by examiner

INTER-OPERABLE CAPSULE DISPENSING UNIT AND BEVERAGE PREPARATION MACHINE

CROSS-REFERENCE TO RELATED APPLICATIONS/INCORPORATION BY REFERENCE STATEMENT

This application is a US national stage application filed under 35 USC § 371 of International Application No. PCT/EP2015/069141, filed Aug. 20, 2015; which claims priority to EP App No. 14181722.1, filed Aug. 21, 2014. The entire contents of the above-referenced patent applications are hereby expressly incorporated herein by reference.

TECHNICAL FIELD

The presently disclosed and/or claimed inventive concept(s) relates to a system for the preparation of a beverage, the system comprising a beverage preparation machine, a capsule and a capsule dispenser to dispense a capsule from a repository thereof, wherein the beverage preparation machine comprises an extraction unit to extract an ingredient of the beverage from the capsule during preparation of the beverage and the capsule dispenser is operatively linked to the beverage preparation machine.

BACKGROUND

Increasingly machines for the preparation of a beverage are configured to operate using a capsule that comprises a dosage of an ingredient of the beverage, for instance, coffee, tea or soup. During preparation an extraction unit of the machine at least partially extracts the ingredient from the capsule, e.g. by dissolution. Examples of such machines are provided in EP 2393404 A1, EP 2470053 A1, EP 2533672 A1, EP 2509473 A1 EP 2685874 A1. The increased popularity of these machines may be partly attributed to enhanced user convenience compared to a conventional beverage preparation machine, e.g. a stove-top espresso maker or a manually operated cafetiére (french press). It may also be partly attributed to an enhanced brewing process of the machine, wherein: the capsule is inserted into a extraction unit; heated water is injected into an inlet made in the capsule; the ingredient within the capsule is extracted by the heated water through an outlet made in the capsule; a brewed beverage is collected from the outlet heated water. During this process operational parameters of the machine can be tailored to the specific capsule and/or ingredients therein to enhance the taste of the beverage. For example, the operational parameters may comprise: water temperature at inlet and outlet; pre-wetting duration; water flow rate; water quantity; other operations during the brewing process. In this way the brewing process is optimised.

The said beverage machines can be adapted for use in public or commercial establishments by the association with a capsule dispensing unit, from which a user is operable to select and/or purchase a capsule from a repository thereof. There is a need for interoperability of such capsule dispensers and beverage preparation machines to control capsule dispensing and beverage preparation operations e.g.: to restrict users stockpiling discounted capsules, which have been dispensed from the capsule dispenser, for use on an unrelated beverage dispensing machine; to restrict capsules not dispensed from the capsule dispenser being used on the beverage preparation machine.

In general it may be undesirable to provide the said interoperability by integrating the capsule dispenser and beverage preparation machine such that dispensed capsules are immediately extracted, this is because: a single capsule dispenser may be used to supply numerous beverage preparation machines; integrating a capsule dispenser on an existing machine may not be desirable, e.g. for reasons of cost; there may be a range of different beverage preparation machines available to the user, whereby the user selects a preferred machine, e.g. a machine with particular beverage preparation options.

U.S. Pat. No. 7,197,377 discloses a system wherein a consumable item, such as a capsule or a container thereof, is supplied from a supplier (rather than a capsule dispenser). The capsule comprises an identifier such as a code e.g. a barcode, RFID or other suitable code. The beverage preparation machine comprises a code reader to identify the capsule by reading the said code of the identifier and is configured to increment a number of authorised extraction processes accordingly. If there are no authorised extraction processes then the beverage preparation machine can be prevented from executing an extraction process. WO 2005104911 discloses a capsule dispensing unit however there is no interoperability with an associated beverage preparation machine.

A drawback of this system is that the capsules require an identifier and the beverage preparation machine must comprise a code reader operable to identify the identifier. Accordingly the system can be expensive and complicated to operate, it may also be complicated to retrofit to existing systems.

BRIEF DESCRIPTION OF THE DRAWINGS

For a better understanding of the presently disclosed and/or claimed inventive concept(s), and to show how embodiments of the same may be carried into effect, reference will now be made, by way of example, to the accompanying diagrammatic drawings in which:

DETAILED DESCRIPTION

Figure 1:
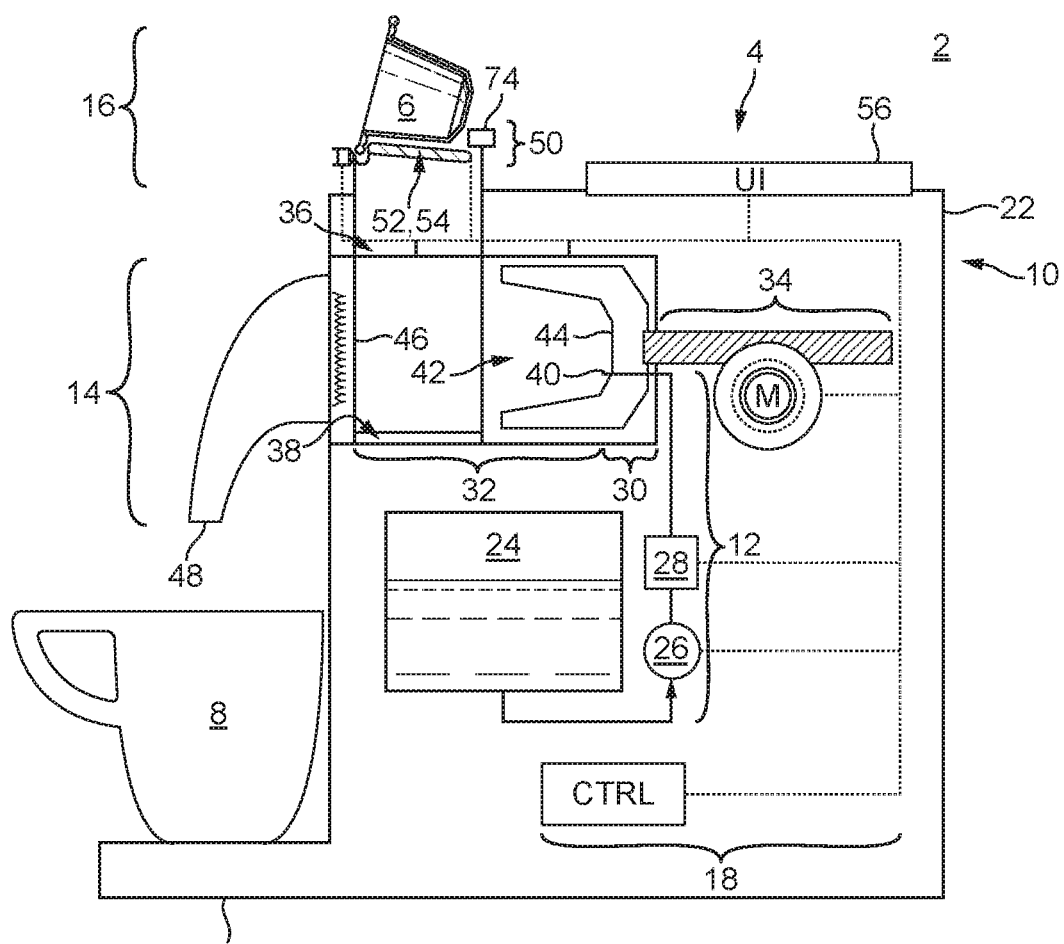
FIG. 1 is an illustrative view of a general beverage preparation machine, a capsule and a receptacle of a beverage preparation system.

One non-limiting object of the presently disclosed and/or claimed inventive concept(s) is to provide a system that comprises a beverage preparation machine and capsule dispenser from which a capsule is dispensed and supplied by a user to the beverage preparation machine, wherein the system is operable restrict capsule dispensing and operation of the beverage preparation machine.

It would be advantageous to provide a system that is operable to restrict users stockpiling discounted capsules, which have been dispensed from the capsule dispenser, for use on an unrelated beverage dispensing machine.

It would be advantageous to provide a system that is operable to restrict the use of capsules not dispensed from the capsule dispenser on the beverage preparation machine.

It would be advantageous to provide a system that is cost-effective.

It would be advantageous to provide a system that is safe and convenient to use.

It would be advantageous to provide an arrangement that can function with the above objective that is conveniently retrofittable to an existing system.

Objects of the presently disclosed and/or claimed inventive concept(s) are achieved by the beverage preparation system according to claim 1, the capsule dispenser according to claim 11, the beverage preparation machine according to claim 12, the method according to claim 13 and the computer program according to claim 14.

Disclosed herein and according to a first aspect of the presently disclosed and/or claimed inventive concept(s) is a beverage preparation system comprising: a capsule dispenser to dispense a capsule to a user as a dispensing operation, which is initiated by a user (e.g. by the input of a command into a user interface or the actuation of a mechanical device); a beverage preparation machine to extract an ingredient of a beverage from a capsule supplied thereto by a user (e.g. a user manually loads or supplies a capsule into/to the beverage preparation machine for extraction) as a beverage preparation operation, the capsule dispenser and beverage preparation machine being operatively linked (e.g. by wired or wireless media directly) via a control system (the control system may comprise various arrangements e.g. it can be located on one or both of the beverage preparation machine and the capsule dispenser or be separate therefrom and exchange information and/or signals to control the associated components). The control system is configured to: obtain dispensing information (e.g. via a command from a user interface or via a sensor of the capsule dispenser or over a communication interface or via a computer program of the capsule dispenser) comprising information relating to a said dispensing operation, the dispensing information for determining a dispensing count, which comprises a running count of the capsule dispensing operations; preferably (in certain non-limiting embodiments) determine said dispensing count (or an equivalent count) from the dispensing information; obtain beverage preparation information (e.g. via a command from a user interface or via a sensor of the beverage preparation machine or over a communication interface or via a computer program of the beverage preparation machine) comprising information relating to a said beverage preparation operation, the beverage preparation information for determining a beverage preparation count, which comprises a running count of the beverage preparation operations; preferably (in certain non-limiting embodiments) determine said beverage preparation count (or an equivalent count) from the beverage preparation information. The control system being further configured to disable a subsequent beverage preparation operation according to the condition (which includes all functionally equivalent conditions): IF the dispensing count is less than or equal to beverage preparation count or IF the dispensing count is less than the beverage preparation count by more than a first predetermined amount. Generally the first and second logic conditions are not implemented on the same system i.e. they are mutually exclusive and are alternative options.

A functionally equivalent condition comprises any mathematical inequality that provides the same functional result. As an example a system count can be derived, whereby the system count is incremented by a predetermined amount such as 1 for each dispensing operation and decremented by the predetermined amount for each beverage preparation. In this way the system count is effectively derived by the sum of the aforesaid dispensing count and beverage preparation count. A functionally equivalent condition using the system count is: disable a subsequent beverage preparation operation IF system count is less than or equal to 0 or less than 0 by more than the first predetermined amount.

Advantageously objects of the presently disclosed and/or claimed inventive concept(s) are solved since the above mathematical inequalities enables control of the beverage preparation system to restrict the use of capsules not dispensed from the capsule dispenser in the beverage preparation machine, e.g.: if the dispensing count is less than the beverage preparation count then more beverages have been prepared than capsules dispensed, and in response the beverage preparation machine is disabled to prevent further beverage preparation operations; if the dispensing count is equal to the beverage preparation count the same amount of beverages have been prepared as capsules dispensed (including zero), and in response the beverage preparation machine is disabled to prevent further beverage preparation operations until a capsule is dispensed. In a further example of this configuration, if the dispensing count is or less than the beverage preparation count by more than the first predetermined amount (a non-zero positive amount such as 1 or 2 or 3 or more) then the beverage preparation machine is disabled. In this way the beverage preparation machine can be controlled to allow a small amount of capsules (which is the first predetermined amount) to be used in the beverage preparation machine, wherein the said capsules were either: not dispensed from the capsule dispenser; or were dispensed from the capsule dispenser but were not used within a predetermined amount of time from their said dispensing such that counter reset occurred before their use.

Moreover the above system can be cost-effectively implemented on existing beverage preparation systems without the requirement of capsule recognition according to the prior art, the latter being expensive to implement.

Accordingly, the control system may be configured to enable a subsequent beverage preparation operation according to the condition (which includes all functionally equivalent conditions): IF the dispensing count is greater than the beverage preparation count or IF the dispensing count is less than the beverage preparation count by less than or equal to the first predetermined amount. This condition sets a part of a region of feasibility (wherein the beverage preparation machine is enabled) the other side of which is the initial condition of the first aspect (wherein the beverage preparation machine is disabled). An example of a functionally equivalent condition using the aforesaid system count is: enable the beverage preparation operation IF system count is greater than 0 or less than 0 by less than or equal to the first predetermined amount.

In response to the aforesaid inequality, a subsequent capsule dispensing operation may be enabled or disabled, e.g.:

The control system is configured to enable a subsequent capsule dispensing operation according to the condition (which includes all functionally equivalent conditions): IF the dispensing count is less than or equal to beverage preparation count or IF the dispensing count is less than beverage preparation count by more than the first predetermined amount. In this way the capsule dispenser is enabled if the dispensing count is generally less than the beverage preparation count to enable the deficit of capsules to be dispensed so that the beverage preparation machine becomes enabled (in accordance with the aforementioned region of feasibility).

Alternately, the control system is configured to disable a subsequent capsule dispensing operation according to the condition (which includes all functionally equivalent conditions): IF the dispensing count is less than or equal to the beverage preparation count or IF the dispensing count is less than beverage preparation count by more than the first predetermined amount. In this way the capsule dispenser can be permanently disabled if the dispensing count is generally less (e.g. by more than the first predetermined amount) than the beverage preparation count, and may for example require re-setting by an administrator.

The control system may be configured to disable a subsequent capsule dispensing operation according to the condition (which includes all functionally equivalent conditions): IF dispensing count is greater than or equal to the sum of the beverage preparation count and a second predetermined amount. An example of a functionally equivalent condition using the aforesaid system count is: disable the dispensing operation IF system count is greater than or equal to the second predetermined amount.

Advantageously objects of the presently disclosed and/or claimed inventive concept(s) are solved since the above mathematical inequality enables control of the beverage preparation system to restrict the accumulating of capsules dispensed from the capsule dispenser without use on the beverage preparation machine, e.g.: a user may stockpile discounted capsules for use on other beverage preparation machines or may purchase the remaining stock of a particular favoured type of capsule. In particular, if the dispensing count is equal to the beverage preparation count plus the second predetermined amount, (which may be set at any suitable non-zero positive value, e.g. 2-50, such as (but not limited to) a number equal to more than 1 or 5 or 10 or 20), then a stockpile of capsules of size the second predetermined amount has been accumulated, thus the dispensing operation can be disabled to prevent the accumulation of a stockpile of capsules of size greater than the second predetermined amount.

Accordingly, the control system may be configured to enable a subsequent capsule dispensing operation according to the condition (which includes all functionally equivalent conditions): IF dispensing count is less than the sum of the beverage preparation count and a second predetermined amount. This condition sets a part of a region of feasibility (wherein the capsule dispenser is enabled) the other side of which is the aforesaid converse condition (wherein the capsule dispenser is disabled). An example of a functionally equivalent condition using the aforesaid system count is: enable the dispensing operation IF system count is less than the second predetermined amount.

In response to the aforesaid inequality, a subsequent beverage preparation operation may be enabled or disabled, e.g.:

The control system is configured to disable a subsequent beverage preparation operation according to the condition (which includes all functionally equivalent conditions): IF dispensing count is greater than or equal to the sum of the beverage preparation count and a second predetermined amount. In this way the beverage preparation machine is permanently disabled in the event of excessive accumulation of capsules, and may for example require re-setting by an administrator.

Alternatively the control system is configured to enable a subsequent beverage preparation operation according to the condition (which includes all functionally equivalent conditions): IF dispensing count is greater than or equal to the sum of the beverage preparation count and a second predetermined amount. In this way the beverage preparation machine is enabled in the event of excessive accumulation of capsules to enable the said accumulation of capsules to be used up so that the capsule dispenser becomes enabled once again.

The above conditions may be suitably combined, e.g. such that the control system is configured to control the beverage preparation system with the following inequality: the control system is configured to disable a subsequent beverage preparation operation according to the condition (which includes all functionally equivalent conditions): IF the dispensing count is less than or equal to the beverage preparation count or IF the dispensing count is less than the beverage preparation count by more than a first predetermined amount; the control system may be configured to enable a subsequent beverage preparation operation according to the condition (which includes all functionally equivalent conditions): IF the dispensing count is greater than the beverage preparation count or IF the dispensing count is less than the beverage preparation count by less than or equal to the first predetermined amount; the control system is configured to disable a subsequent capsule dispensing operation according to the condition (which includes all functionally equivalent conditions): IF the dispensing count is greater than or equal to the beverage preparation count by a second predetermined amount; the control system may be configured to enable a subsequent capsule dispensing operation according to the condition (which includes all functionally equivalent conditions): IF dispensing count is greater than the beverage preparation count by less than the second predetermined amount; otherwise one or both of the beverage preparation operations and capsule dispensing operations may be disabled.

The control system may be configured to set the dispensing count and/or the beverage preparation count to a predetermined amount according to the condition (which includes all functionally equivalent conditions such as setting an equivalent count that can be derived from said counts e.g. the aforesaid system count, to a predetermined amount): IF a predetermined amount of time lapses following a dispensing operation without a beverage preparation operation. For one or both of said counts the predetermined amount is typically 0, but may as an example be 1 or −1 or 2 or −2. Generally the counts are returned to a start condition. The predetermined amount of time is typically 2 or 5, or 10, or 30, or 60 minutes. Advantageously, a user has the said predetermined amount of time to use the capsule otherwise the capsule dispensing count it is reset and the capsule is considered not to have been dispensed. Both counters may be reset after the said predetermined amount of time to ensure the beverage preparation system is not permanently disabled.

The aforesaid control system can comprises various equivalent arrangements, e.g.: a single control system that is operable to control the capsule dispenser and beverage preparation machine; a general control system that is operable to interface with a sub-control system of the capsule dispenser and a sub-control system of the beverage preparation machine; a general control system of the capsule dispenser which is operable to interface with a sub-control system of the beverage preparation machine and the converse. More particularly: a control system of the capsule dispenser comprises a processing unit and a communication interface that is operable for data exchange with a corresponding communication interface and processing unit of a sub-control system of the beverage preparation machine; or the converse; or a control system of the capsule dispenser comprises a processing unit and a communication interface for controlling directly (i.e. without a further processing unit) the electrically operated components of the beverage preparation machine or the converse.

The disabling of the beverage preparation machine by the control system can be achieved by various means, e.g.: the control system controls an electrically operated capsule holder loading mechanism of the extraction unit of the beverage preparation machine to move to a capsule extraction position, such that a user is prevented from inserting a capsule therein; the control system effects null operation electronically operated components of the beverage preparation machine, e.g. the fluid supply system. The disabling of the capsule dispenser can be achieved by various means, e.g.: the control system effect null operation of an electrically operated component of the capsule dispenser, e.g. a capsule dispensing system of the capsule dispenser; the control system effects a mechanically operated capsule dispensing system of the capsule dispenser to be blocked from being actuatable by the user, such as by means of a solenoid to engage a component associated therewith.

The beverage preparation machine and capsule dispenser may be operatively linked via the aforesaid control system by a communication interface of the control system comprising cabled or wireless media, e.g.: a wired connection such as RS-232, USB, I²C, Ethernet define by IEEE 802.3; a wireless connection, such as wireless LAN (e.g. IEEE 802.11) or a near filed system. The beverage preparation machine and capsule dispenser may be mechanically connected to each other, e.g.: they are arranged within the same housing or are connected to the same body.

Generally the capsule dispenser and the beverage preparation machine are arranged in operational proximity to each other, e.g. such that a user can shortly after dispensing a capsule insert the said capsule into the beverage preparation machine, they may for example be in the same room or be arranged within a line of sight of each other.

The control system may be configured to disable the beverage preparation machine or the capsule dispenser if the other of the beverage preparation machine or capsule dispenser is operatively disconnected from the control system via the communication interface, whereby operatively disconnected may for example comprise the physical disconnection or loss of the ability for data exchange, e.g. if the communication interface is not powered-up or the associated beverage preparation machine and/or capsule dispenser is not powered-up. With such a configuration the disconnected beverage preparation machine or the capsule dispenser may be configured to default to a disabled state. In this way the beverage dispensing system is configured such that a capsule can only be dispensed and extracted if both the beverage preparation machine and capsule dispenser are connected to the control system via the communication interface.

The beverage preparation system may comprise a plurality of beverage preparation machines which are operatively connected to the control system, the control system configured to receive beverage preparation information from each of the beverage preparation machines, and for determining therefrom a single aggregate beverage preparation count comprising a running count of the beverage preparation operations for the plurality of beverage preparation machines. In such a system there is generally only a single capsule dispenser connected to the control system.

The control system may be configured to set the dispensing count and/or the beverage preparation count or an equivalent count that can be derived therefrom to the aforesaid predetermined amount if for all of the said beverage preparation machines the aforesaid predetermined amount of time lapses following a dispensing operation without a beverage preparation operation. In the event of disabling the beverage preparation operation, the control system may be operable to effect the disabling of the said operation on all of the beverage preparation machines.

The beverage preparation system may be operable to communication with a server system via a communication interface of the control system, e.g. a communication interface of the beverage preparation machine and/or the capsule dispenser. The server system may be used to monitor/adjust operational parameters of the beverage preparation machine and/or the capsule dispenser, e.g.: one or both of the associated counts, and in particular a setting of a count to the said predetermined amount or other adjustment of a count; parameters associated with the extraction process, such as water temperature or capsule consumption for re-ordering.

The control system comprises a user interface, which may be discrete from the capsule dispenser and the beverage preparation machine, or may be arranged fully or partly on the capsule dispenser and/or the beverage preparation machine (e.g.: the sub-control system that controls the capsule dispenser comprise part or all of the user interface and the sub-control system that controls the beverage preparation machine comprises part or all of the user interface). The user interface is generally operable to receive an input from a user to dispense a capsule, i.e. a dispensing operation. The control system in response is operable to execute the dispensing operation, which is the dispensing of a capsule via a capsule dispensing unit of the capsule dispenser. The control system may comprise a sensor to detect a dispensed a capsule, such as a photodiode, inductive sensor, or other suitable sensor. The user interface is generally operable to receive an input from a user to prepare a beverage, i.e. a beverage preparation operation. The control system in response is operable to effect the preparation of a beverage by generally controlling the: extraction unit; fluid supply; capsule processing unit (when present). The control system may comprise a sensor to detect a successful preparation of a beverage, such as a photodiode, inductive sensor, flow rate sensor or other suitable sensor.

The user interface may comprise an identification system, such as a key pad or magnetic strip reader for use with a key card, which is operable to authenticate an identity of a user. The control system may be configured to enable particular operations of the capsule dispenser and/or beverage preparation machine related to an identified user, e.g. the purchasing of particular capsules; the purchasing of capsules at a particular price; the subtraction of a price of a capsule from credit associated with the user; administrator operations, such as reset of a count or other servicing/administrative related operations.

The control system comprises one or more processing units for receiving commands from a user and control of the aforesaid components, e.g.: a processing unit of the capsule dispenser may receive an input from the user interface, sensors and communication interface and in response may send an output to the capsule dispensing unit and a processing unit of the beverage preparation machine; a processing unit of the beverage preparation machine may receive an input from a communication interface, the user interface and in response may effect control of the extraction unit and fluid supply to execute an extraction process.

Disclosed herein according to a second aspect of the presently disclosed and/or claimed inventive concept(s) is a capsule dispenser of a beverage preparation system that comprises the capsule dispenser and a beverage preparation machine to extract an ingredient of a beverage from a capsule supplied thereto by a user as a beverage preparation operation, the capsule dispenser to dispense a capsule to a user as a dispensing operation. The capsule dispenser comprising a control system configured to obtain dispensing information for determining a dispensing count. The dispensing count comprising a running count of the capsule dispensing operations. Generally the capsule dispenser determines the dispensing count (or an equivalent count) from the dispensing information, which preferably (in certain non-limiting embodiments) comprises information relating to a said dispensing operation. The control system is further configured to obtain (i.e. over a communication interface) beverage preparation information for determining a beverage preparation count. In certain non-limiting embodiments, the control system determines said dispensing count (or an equivalent count) therefrom. Generally the received beverage preparation information comprise information relating to a said beverage preparation operation. Alternatively it may obtain (i.e. over a communication interface) beverage preparation count (or an equivalent count), which comprises a running count of the beverage preparation operations. The control system is further configured to effect the disabling of a subsequent beverage preparation operation according to the condition (which includes all functionally equivalent conditions): IF dispensing count is less than or equal to beverage preparation count or less than the beverage preparation count by more than a first predetermined amount. The capsule dispenser may comprise and/or be configured to operate in accordance with any feature of the first aspect.

Disclosed herein according to a third aspect of the presently disclosed and/or claimed inventive concept(s) is a beverage preparation machine of a beverage preparation system that comprises a capsule dispenser to dispense a capsule to a user as a dispensing operation, the beverage preparation machine to extract an ingredient of a beverage from a capsule supplied thereto by a user as a beverage preparation operation. The beverage preparation machine comprising a control system configured to obtain (i.e. over a communication interface) dispensing information for determining a dispensing count. In certain non-limiting embodiments, the beverage preparation machine determines the dispensing count (or an equivalent count) therefrom. Generally the received dispensing information comprise information relating to a said capsule dispensing operation. Alternatively it may obtain (i.e. over a communication interface) a dispensing count (or an equivalent count), which comprises a running count of the capsule dispensing operations. The control system is further configured to obtain beverage preparation information for determining a beverage preparation count. The beverage preparation count comprising a running count of the beverage preparation operations. Generally the beverage preparation machine determines the beverage preparation count from beverage preparation information comprising information relating to a said beverage preparation operation. The control system is further configured to disable a subsequent beverage preparation operation according to the condition (which includes all functionally equivalent conditions): IF dispensing count is less than or equal to beverage preparation count or less than the beverage preparation count by more than a first predetermined amount. The beverage preparation machine may comprise and/or be configured to operate in accordance with any feature of the first aspect.

Disclosed herein according to a fourth aspect of the presently disclosed and/or claimed inventive concept(s) is a method of preparing a beverage using the beverage preparation system according to any feature of the first aspect of the presently disclosed and/or claimed inventive concept(s), the method comprising: obtaining dispensing information for determining a dispensing count, which comprises a running count of the capsule dispensing operations and preferably (in certain non-limiting embodiments) derive therefrom the dispensing count (or an equivalent count); obtaining beverage preparation information for determining a beverage preparation count, which comprises a running count of the beverage preparation operations and preferably (in certain non-limiting embodiments) derive therefrom the beverage preparation count (or an equivalent count); disabling a subsequent beverage preparation operation according to the condition (which includes all functionally equivalent conditions): IF dispensing count is less than or equal to beverage preparation count or less than beverage preparation count by more than a first predetermined amount.

Disclosed herein according to a fifth aspect of the presently disclosed and/or claimed inventive concept(s) is a computer program for a processing unit of a control system of a beverage preparation system, the beverage preparation system comprises a capsule dispenser to dispense a capsule to a user as a dispensing operation a beverage preparation machine to extract an ingredient of a beverage from a capsule supplied thereto by a user as a beverage preparation operation. The computer program preferably (in certain non-limiting embodiments) comprises program code and/or program logic. The computer program is executable (e.g. by the processor) to: obtain dispensing information for determining a dispensing count or obtain a dispensing count, which comprises a running count of the capsule dispensing operations; obtain beverage preparation information for determining a beverage preparation count or obtain a dispensing count, which comprises a running count of the beverage preparation operations; disable a subsequent beverage preparation operation according to the condition (which includes all functionally equivalent conditions): IF dispensing count is less than or equal to beverage preparation count or less than the beverage preparation count by more than a first predetermined amount. The computer program may be configured to operate in accordance with any feature of the first aspect.

Disclosed herein according to an sixth aspect of the presently disclosed and/or claimed inventive concept(s) is provided a non-transitory computer readable medium comprising the computer program according to the fifth aspect. The non-transitory computer readable medium may comprise a memory unit of the processor or other computer-readable storage media for having computer readable program code for programming a computer stored thereon, e.g. a hard disk, a CD-ROM, an optical storage device, a magnetic storage device, Flash memory.

The above aspects of the presently disclosed and/or claimed inventive concept(s) may be combined in any suitable combination. Moreover, various features herein may be combined with one or more of the above aspects to provide combinations other than those specifically illustrated and described. Further objects and advantageous features of the presently disclosed and/or claimed inventive concept(s) will be apparent from the claims, from the detailed description, and annexed drawings.

Beverage Preparation System

FIG. 1 shows an illustrative view of part of a beverage preparation system 2, which comprises at a first level: a beverage preparation machine 4; a capsule 6; a receptacle 8; capsule dispenser (discussed and shown later).

Beverage Preparation Machine

With further reference to FIG. 1, initially the beverage preparation machine 4 will be described. Functionally, the beverage preparation machine 4 is operable to extract one or more ingredients from the capsule 6 by means of the injection of fluid in to the capsule, whereby the extracted ingredient forms at least part of a beverage collected in the receptacle 8 (e.g. a cup). The beverage preparation machine 4 may be dimensioned for use on a work top, i.e. it is less than 50 cm in length, width and height or to operate as part of a freestanding unit. Examples of suitable beverage preparation machines 4 are disclosed in EP 2393404 A1, EP 2470053 A1, EP 2533672 A1, EP 2509473 A1 EP 2685874 A1, all of which are incorporated herein by reference. For completeness such a beverage preparation machine 4 will now be described in more detail, and can be considered to comprise at a first level of the beverage preparation machine 4: a housing 10; a fluid supply 12; an extraction unit 14; optionally a capsule processing unit 16; a control system 18. These components will now be sequentially described:

Housing of Beverage Preparation Machine

The housing 10 houses and supports the aforementioned first level components and comprises at a second level of the beverage preparation machine 4: a base 20 and a body 22. The base 20 being for abutment with a support surface. The body 22 being for mounting thereto the other first level components.

Fluid Supply of Beverage Preparation Machine

The fluid supply 12 is operable to supply fluid, which is in general water that is heated, to the extraction unit 14. The fluid supply 12 typically comprises at a second level of the beverage preparation machine 4: a reservoir 24 for reservoir containing fluid, which in most applications is 1-2 litres of fluid; a fluid pump 26, such as a reciprocating or rotary pump; a fluid heater 28, which generally comprises a thereto block type heater; an outlet for supplying the fluid to the extraction unit 14, which will be discussed. The reservoir 24, fluid pump 26, fluid heater 28, and outlet are in fluid communication with each other in any suitable order. In an alternative example the fluid supply 12 may comprise a connection to an external fluid source e.g. a water main.

Extraction Unit of Beverage Preparation Machine

The extraction unit 14 is operable to receive and process the capsule 6 to extract an ingredient therefrom. The extraction unit 14 can be arranged to receive the capsule 6 directly from a user, or to receive the capsule 6 from the optional capsule processing unit 16. The extraction unit 14 is operable to move between a capsule receiving position and a capsule extraction position, when moving from the capsule extraction position to the capsule receiving position, the extraction unit may be moved through or to a capsule ejection position, wherein a spent capsule can be ejected therefrom. The extraction unit typically comprises at a second level of the beverage preparation machine 4: an injection head 30; a capsule holder 32; a capsule holder loading mechanism 34; a capsule insertion channel 36; a capsule ejection channel 38, which are sequentially described:

The injection head 30 is configured to inject fluid into a cavity of the capsule 6 when held by the capsule holder 32, and to this end has mounted thereto an injector 40, which has a nozzle that is in fluid communication with the outlet of the fluid supply 12. The injection head 30 generally comprises a lance, or other suitable member, with the injector 40 extending therethrough, for perforation of the capsule 6 to form an inlet to the said cavity.

The capsule holder 32 is configured to hold the capsule during extraction and to this end it is operatively linked to the injection head 30. The capsule holder 32 is operable to move to implement the said capsule receiving position and capsule extraction position: with the capsule holder 32 in the capsule receiving position (as shown in FIG. 1) a capsule 6 can be supplied to the capsule holder 32 from the capsule insertion channel 36; with the capsule holder 32 in the capsule extraction position a supplied capsule is held by the holder, the injection head 30 can inject fluid into the cavity of the held capsule, and one or more ingredients can be extracted therefrom. When moving the capsule holder 32 from the capsule extraction position to the capsule receiving position, the capsule holder 32 can be moved through or to the said capsule ejection position, wherein a spent capsule can be ejected from the capsule holder 32 via the capsule ejection channel 38. The capsule holder 32 generally comprises: a cavity 42 with a cavity base 44 comprising the injection head 30 mounted thereto; an extraction wall 46 having an outlet 48 for the extracted ingredients. To implement the said capsule receiving and the capsule extraction positions the extraction wall 46 and cavity 42 can be moveable relative to each other, e.g. the extraction wall 46 is fixed to the body 22 and the cavity 42 is movable relative thereto. In another example the cavity can be fixed to the extraction wall and to implement the capsule receiving and capsule extraction positions the injection head and base of the cavity are movable relative the cavity: an example of such a system is provided in WO 2009/113035, which is incorporated herein by reference.

The capsule holder loading mechanism 34 is operable to drive the capsule holder 32 between the said capsule receiving position and the capsule extraction position. To this end the capsule holder loading mechanism 34 typically comprises a linear actuator, such as a motor or solenoid, and an actuatable mechanism, such as a rack and pinion arrangement. The capsule holder loading mechanism 34 may alternatively be mechanically actuated, e.g. by an arrangement of linkages as disclosed in WO 2009/113035, which comprises a user actuated arrangement.

The extraction unit 14 can operate by means of injection of fluid at pressure into the cavity of the capsule 6, e.g. at up to 20 bar, which can be achieved by means of the injection head 30 and pump 26, as in the illustrated example. It may alternatively operate by centrifugation as disclosed in EP 2594171 A1, which is incorporated herein by reference. In the example of the latter the extraction unit 14 further comprises a capsule drive mechanism, which typically comprises an electric motor and drive train, configured to rotate a capsule support to effect the said centrifugation.

Capsule Processing Unit of Beverage Preparation Machine

The beverage preparation machine 4 may comprise a capsule processing unit 16. The capsule processing unit 16 is operable to process a capsule 6 to: detect its supply by a user; optionally identify a type of the capsule 6; optionally read a code of the capsule; transfer the capsule 6 to the extraction unit 14. Generally, the capsule processing unit 16 is arranged above the extraction unit 14 and is integrated as part of the body 22 of the beverage preparation machine 4 with its various sub components attached thereto. The capsule processing unit 16 comprises at a second level of the beverage preparation machine 4: optionally a code reading system 50; a capsule transfer mechanism 52; a capsule detection system 54, which are sequentially described:

The code reading system 50 is operable to read a code of the capsule 6 to generate therefrom a code signal. The code signal can be processed by the processing unit (discussed later on) of the control system 18 to determine extraction information. The extraction information encoded by the code relates to the capsule and/or operational parameters of the machine that may be used during the extraction process. For example, the extraction information may encode one or more of the following: angular velocity/acceleration (for centrifugally operated extraction units); water temperature (at capsule inlet and/or machine outlet); water mass/volumetric flow rate; water volume; a sequence of extraction operations e.g. pre-wetting time; capsule parameters (volume, type, capsule identifier, expiry date), which may for example be used to monitor capsule consumption for the purpose of capsule re-ordering.

The code reading system 50 comprises a code reader, which is operable to read a code of the capsule 6. Various code and code reading system 50 configurations may be used, e.g.: an optically readable code and optical reader; an induction based code and an inductive sensor code reader; an RFID tag and interrogating EM field. In code reading system 50 configurations wherein the code is read during relative movement between a reading head of the code reader and the code of the capsule 6, the code reading system 50 comprises a code reading mechanism, which is operable to effect the said relative movement. The code reading system 50 may alternatively be integrated in the extraction unit 14, e.g. in a centrifugation based extraction unit 14, a code of the capsule 6 can be read during the rotation of the capsule.

The capsule transfer mechanism 52 is operable to transfer a processed capsule to the extraction unit 14 (i.e. via the capsule insertion channel 36). Accordingly, it is generally arranged discrete from and above the extraction unit 14. The capsule transfer mechanism 52 effects transfer of a capsule by removal of a constraint constraining the capsule 6 or by displacement of the capsule to the capsule insertion channel 36. In general the capsule transfer mechanism 52 comprises a movable capsule support that is arranged to receive a capsule 6 from a user and is movable relative the body 22, to effect transfer of a capsule supported thereon to the extraction unit 14. More particularly, it is movable between a capsule support position and a capsule transfer position, wherein: when in the capsule support position (as shown in FIG. 1) the code of the capsule 6 can be read by the code reading system 50; when in the capsule transfer position transfer of a supported capsule 6 is effected to the extraction unit 14. The movable capsule support is driven between the positions by means of the capsule support drive mechanism 124, which is in turn driven by the actuator unit. Examples of suitable capsule transfer mechanisms are disclosed in WO 2014/056642 and EP14176243.5, which are incorporated herein by reference.

The capsule detection system 54 is operable to detect the presence, and optionally a type of capsule 6 on the movable capsule support of the capsule transfer mechanism 52. The capsule detection system comprises one or more capsule detection sensors to detect the presence of a capsule in proximity thereto. The capsule detection sensors are operable to generate a capsule detection signal that is processed by the processing unit (discussed later on) of the control system 18. The or each capsule detection sensor can be of various configurations, e.g.: inductive sensors; optical sensors; mechanically actuated sensors.

Control System of Beverage Preparation Machine

Figure 2:
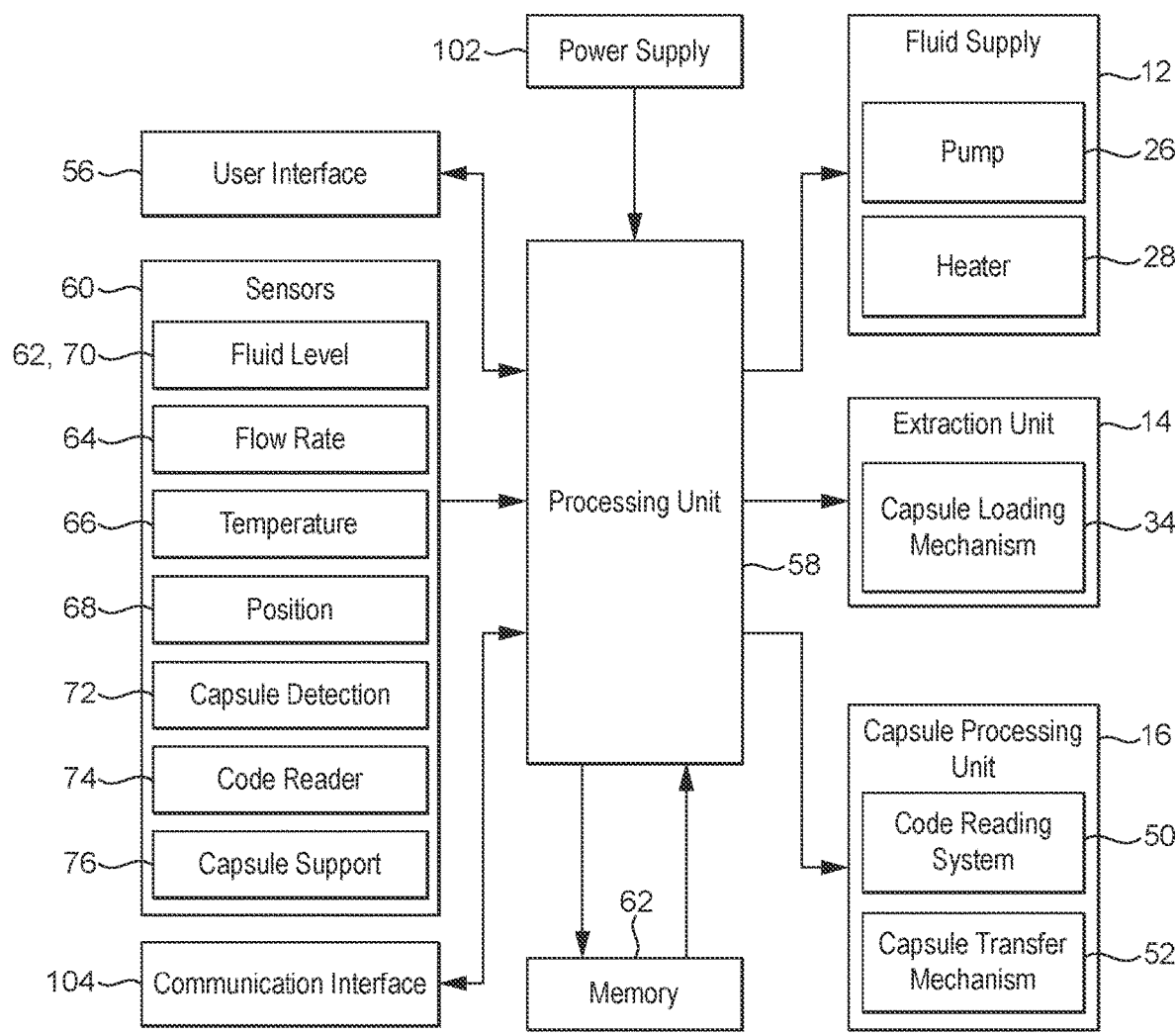
FIG. 2 is a schematic diagram of a control system of the general beverage preparation machine according to FIG. 1.

With reference to FIGS. 1 and 2, the control system 18 will now be considered: the control system 18 is operable to control the other first level components to extract the one or more ingredients from the capsule 6. The control system 18 typically comprises at a second level of the beverage preparation machine 4: a user interface 56; a processing unit 58; optionally sensors 60; a power supply 102; optionally a communication interface 104, which are sequentially described:

The user interface 56 comprises hardware to enable a user to interface with the processing unit 58, by means of a user interface signal. More particularly: the user interface receives commands from a user; the user interface signal transfers the said commands to the processing unit 58 as an input. The commands may, for example, be an instruction to execute an extraction process and/or to adjust an operational parameter of the beverage preparation machine 4 and/or to power on or off the beverage preparation machine 4. The processing unit 58 may also output feedback to the user interface 56 as part of the beverage preparation process, e.g. to indicate the beverage preparation process has been initiated or that a parameter associated with the process has been selected.

The hardware of the user interface 56 may comprise any suitable device(s), for example, the hardware comprises one or more of the following: buttons, such as a joystick button or press button; joystick; LEDs; graphic or character LDCs; graphical screen with touch sensing and/or screen edge buttons. The user interface 56 can be formed as one unit or a plurality of discrete units. For more complicated hardware configurations the user interface 56 can comprise a separate processing unit (examples of which are provided following) to interface with the maser processing unit 58.

The sensors 60 are operable to provide an input signal to the processing unit 58 for monitoring of the extraction process and/or a status of the beverage preparation machine 4. The input signal can be an analogue or digital signal. The sensors 60 typically comprise one or more of the following: fluid level sensors 62 associated with the reservoir 24; flow rate sensors 64 associated with the fluid pump 26; temperature sensors 66 associated with the heater 28; position sensors 68 associated with the extraction unit 14, which are operable to sense the position of the extraction unit 14, (e.g. the capsule receiving position, capsule extraction position, capsule ejection position); fluid level sensors 70 operable to measure a fluid level in the receptacle 6; capsule detection sensors 72 associated with the capsule processing unit 16; the code reader 74 associated with the code reading system 50; a movable capsule support sensor 76 associated with the capsule transfer mechanism 52; angular velocity sensors (for use with extraction units that operate via centrifugation).

The processing unit 58 is operable to: receive an input, i.e. the commands from the user interface 56 and/or the signal of the sensors 60 (e.g. the capsule detection sensors 72 of the capsule detection system 54); process the input according to program code (or programmed logic) stored on a memory unit (discussed later on); provide an output, which is generally an extraction process. More specifically the output comprises the operation of: optionally the capsule processing unit 16 (e.g. operation of the code reading system 50, capsule transfer mechanism 52); the extraction unit 14 (i.e. operation of the capsule holder loading mechanism 34 to drive the capsule holder 32 between the said capsule receiving position and the capsule extraction position); water supply 12 (i.e. operation of the fluid pump 26 and fluid heater 28). Operation of the aforesaid components can be open-loop control, or more preferable (in certain non-limiting embodiments) closed-loop control using the input signal from the sensors 60 as feedback.

The processing unit 58 generally comprise memory, input and output system components arranged as an integrated circuit, typically as a microprocessor or a microcontroller. The processing unit 50 may comprises other suitable integrated circuits, such as: an ASIC; a programmable logic device such as a PAL, CPLD, FPGA, PSoC; a system on a chip (SoC); an analogue integrated circuit, such as a controller. For such devices, where appropriate, the aforementioned program code can be considered programed logic or to additionally comprise programmed logic. The processing unit 50 may also comprise one or more of the aforementioned integrated circuits. An example of the later is several integrated circuits is arranged in communication with each other in a modular fashion e.g.: a slave integrated circuit to control the user interface 42 in communication with a master integrated circuit to control the extraction unit 14 and water supply 12.

The processing unit 58 generally comprises a memory unit 62 for storage of instructions as program code and optionally data. To this end the memory unit typically comprises: a non-volatile memory e.g. EPROM, EEPROM or Flash for the storage of program code and operating parameters as instructions; volatile memory (RAM) for temporary data storage. The memory unit may comprise separate and/or integrated (e.g. on a die of the semiconductor) memory. For programmable logic devices the instructions can be stored as programmed logic.

The instructions stored on the memory unit can be idealised as comprising a beverage preparation program. The beverage preparation program can be executed by the processing unit in response to the said input, (i.e. the commands from the user interface 56 and/or the signal of the capsule detection sensors 72). Execution of the beverage production program causes the processing unit 58 to control the following first level components: optionally the capsule processing unit 16 to process a received capsule to the extraction unit 14; the extraction unit 14 to move between the capsule receiving position and the capsule extraction position; water supply 12 to supply heated water to the extraction unit 14. The beverage preparation program can effect control of the said components using extraction information encoded on the code capsule and/or other information that may be stored as data on the memory unit 62 and/or input via the user interface 56.

The power supply 102 is operable to supply electrical energy to the said controlled components, the processing unit 58 and components associated therewith. The power supply 102 may comprise various means, such as a battery or a unit to receive and condition a mains electrical supply. The power supply 102 may be operatively linked to part of the user interface 56 for powering on or off the beverage preparation machine 4.

The communication interface 104 is for data communication of the beverage preparation machine 4 with another device/system, which may be a server system, a capsule dispenser or other related device. The communication interface 104 can be used to supply and/or receive information related to the beverage preparation process, such as capsule consumption information and/or extraction process information. The communication interface 104 may comprise a first and second communication interface for data communication with several devices at once or communication via different media.

The communication interface 104 can be configured for cabled media or wireless media or a combination thereof, e.g.: a wired connection, such as RS-232, USB, I²C, Ethernet define by IEEE 802.3; a wireless connection, such as wireless LAN (e.g. IEEE 802.11) or near field communication (NFC) or a cellular system such as GPRS or GSM. The communication interface 104 interfaces with the processing unit 58, by means of a communication interface signal. Generally the communication interface comprises a separate processing unit (examples of which are provided above) to control communication hardware (e.g an antenna) to interface with the maser processing unit 58. However, less complex configurations can be used e.g. a simple wired connection for serial communication directly with the processing unit 58.

Capsule of Beverage Preparation System

Figure 3:
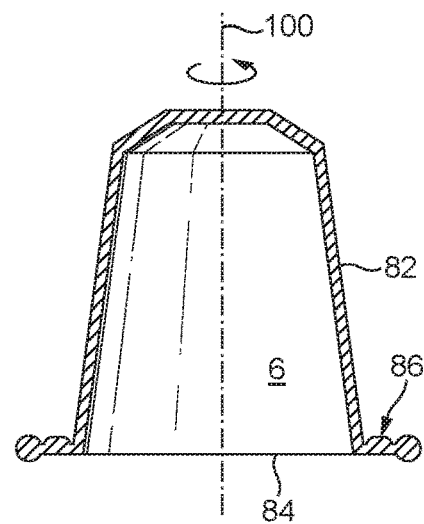
FIG. 3 is a side cross-sectional view of a first embodiment of a capsule of the beverage preparation system according to FIG. 1.

The capsule 6 generally comprises: a body portion defining a cavity for the storage of a dosage of an ingredient to be extracted; a lid portion for closing the cavity; a flange portion for connecting the body portion and flange portion, the flange portion being arranged distal a base of the cavity. The body portion may comprise various shapes, such as a disk, conical or rectangular cross-sectioned shaped. The capsule may be formed from various materials, such as metal or plastic or a combination thereof. In general the material is selected such that it is: food-safe; it can withstand the pressure/temperature of the extraction process; it is perforable to enable insertion of the injector 40 of the injection head 30; it is rupturable for delivery of the extracted ingredient to the outlet 48 of the extraction wall 46. Accordingly, it will be appreciated that the capsule 6 may take various forms, three examples of which are provided in the following:

FIG. 3 shows a side cross-sectional view of a first example of a capsule 6 that comprises: a body portion 82, which comprises a frusta-conically shaped cavity for holding the dosage of the ingredient to be extracted; a lid portion 84 for closing the cavity of the body portion; a flange portion 86 for connection of the body portion 82 and the lid portion 84.

Figure 4:
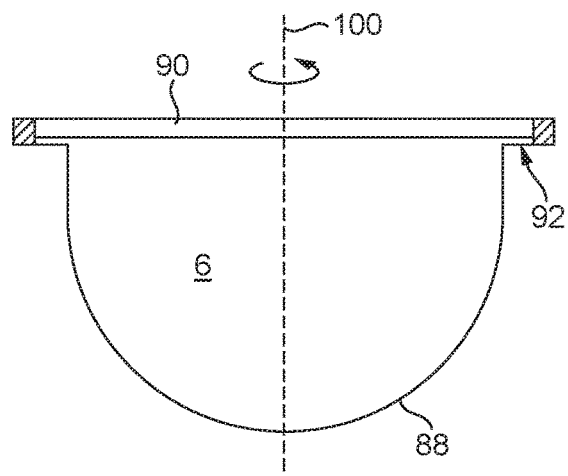
FIG. 4 is a side cross-sectional view of a second embodiment of a capsule of the beverage preparation system according to FIG. 1.

FIG. 4 shows a side cross-sectional view of a second example of a capsule 6 that comprises: a body portion 88, which comprises a hemi-spherically shaped cavity for holding the dosage of the ingredient to be extracted; a lid portion 90 for closing the cavity of the body portion; a flange portion 92 for connection of the body portion 88 and the lid portion 90.

Figure 5:
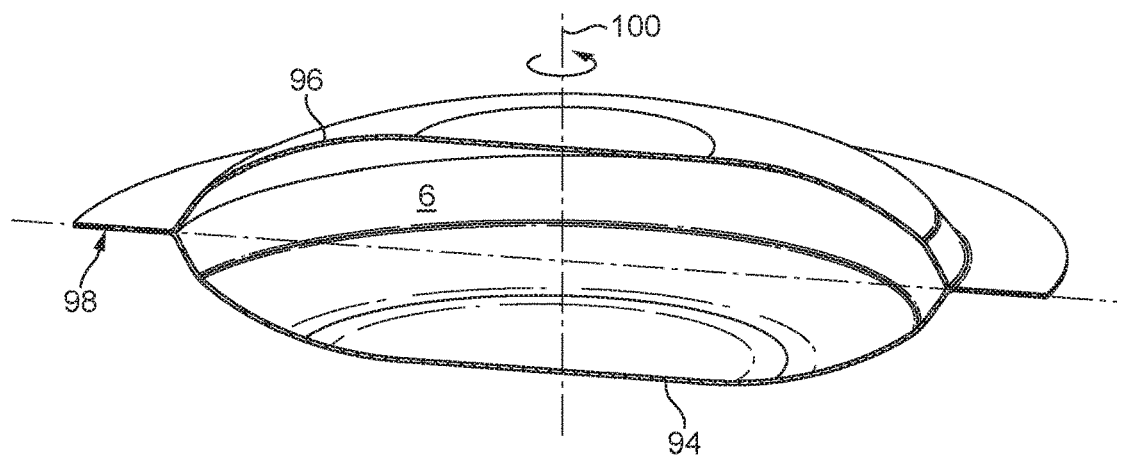
FIG. 5 is a perspective cut-sectional view of a third embodiment of a capsule of the beverage preparation system according to FIG. 1.

FIG. 5 shows a side cross-sectional view of a second example of a capsule 6 that comprises: a body portion 94, which comprises a disc shaped cavity for holding the dosage of the ingredient to be extracted; a lid portion 96, which also comprises a cavity, for closing the cavity of the body portion; a flange portion 98 for connection of the body portion 94 and the lid portion 96.

Generally, the capsule 6 is shaped such that it is substantially rotationally symmetric about a capsule axis of rotation 100 which is extends generally orthogonal to a plane on which the flange portion, 86, 92, 98 is located.

Capsule Dispenser

The capsule dispenser 106 operable to hold a repository of capsules 6, such as 10-300, and is configured to receive an input from a user and in response output a dispensed capsule 6 therefrom, termed herein as a capsule dispensing operation. The capsule dispenser 106 can be integrated with the beverage preparation machine 4 such that they share the same body 22 of the housing 10. Alternatively, it may be separate from the beverage preparation machine 4. To this end the capsule dispenser 106 can be idealised as comprising at a first level of the capsule dispenser 106 a: housing 108; capsule holder 110; capsule dispensing system 112; control system 114, which will be sequentially described.

The housing 108 houses and supports the aforementioned first level components and comprises at a second level of the capsule dispenser 106: a base 116 and a body 118. The base 116 being for abutment with a support surface or the beverage preparation machine 4. The body 118 being for mounting thereto the other first level components.

The capsule holder 110 is for storage of the plurality of capsules 6. Generally the capsules 6 are stored in an ordered manner, for example, stacked or side by side or in strips. Capsules 6 are generally loaded into a body 120 of the capsule holder 110 at a proximal end thereof, or via an opening in the side, and dispensed at a distal end. The capsules 6 may be stored in groups, e.g. by type, by means of one or more cartridge 122 that may be removably attachable to the body 120.

Figure 6:
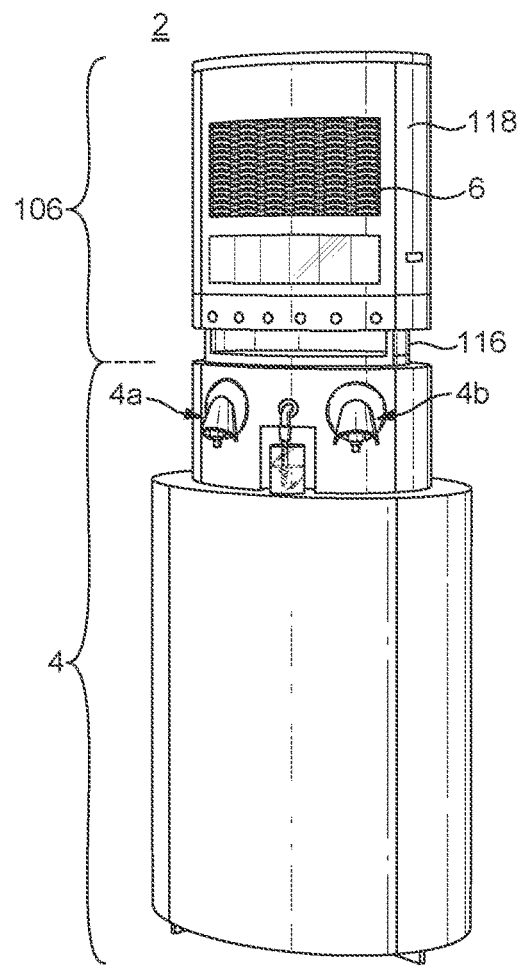
FIG. 6 is an illustrative view of a beverage preparation system that comprises an integrated capsule dispenser and beverage preparation machine.
Figure 7:
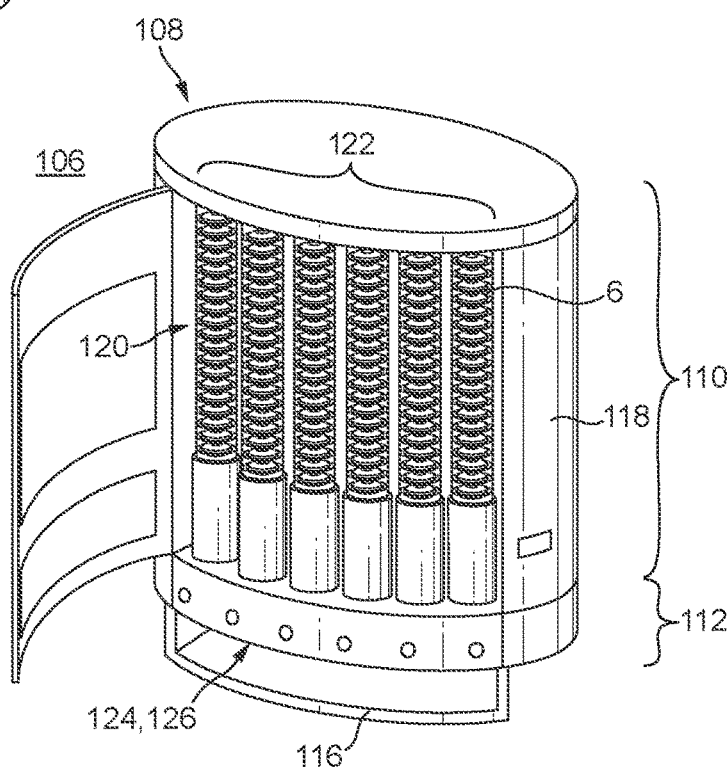
FIG. 7 is an illustrative view of a capsule dispenser of a beverage preparation system.

FIGS. 6 and 7 show an example wherein the capsule dispenser 106 is integrated with the beverage preparation machine 4, and wherein the capsule holder 110 body 120 stows 6 cartridges 122 each storing 10-30 vertically stacked capsules 6. The capsules 6 are dispensed from a distal end of a cartridge 122 and can be loaded into the cartridge 122 at a distal end and/or the proximal end. A cartridge 122 is loaded into the body 120 of the capsule holder 110 via a side door arranged between the proximal and distal ends thereof.

The capsule dispensing system 112 is operable to receive an input to dispense a capsule 6 and in response output the dispensing of a capsule from the capsule dispenser. Generally the capsule dispensing system 112 is an electrically operated mechanism, which is controlled by the control system 114. However, in a more simplistic example it may comprise a user actuated mechanism, e.g. the dispensing mechanism comprises a tray or a rotor which is displaced between a capsule dispensing and capsule retaining position. Referring back to the example of an electrically operated mechanism, the capsule dispensing system 112 comprises: an actuator 124, such as a motor or solenoid, which is controlled by the control system 114; a dispensing mechanism 126 that is operable to move between a capsule dispensing and a capsule retaining position via drive from the actuator 124.

An example of such as system is an actuator comprising a motor that drives a dispensing mechanism that comprises a drive train that is operatively linked to a support member, the support member being driven to extend into and to retract from of the cartridge in the respective capsule retaining and capsule dispensing positions. A more sophisticated example is disclosed in WO 2005/104908, which is incorporated herein by reference.

Figure 8:
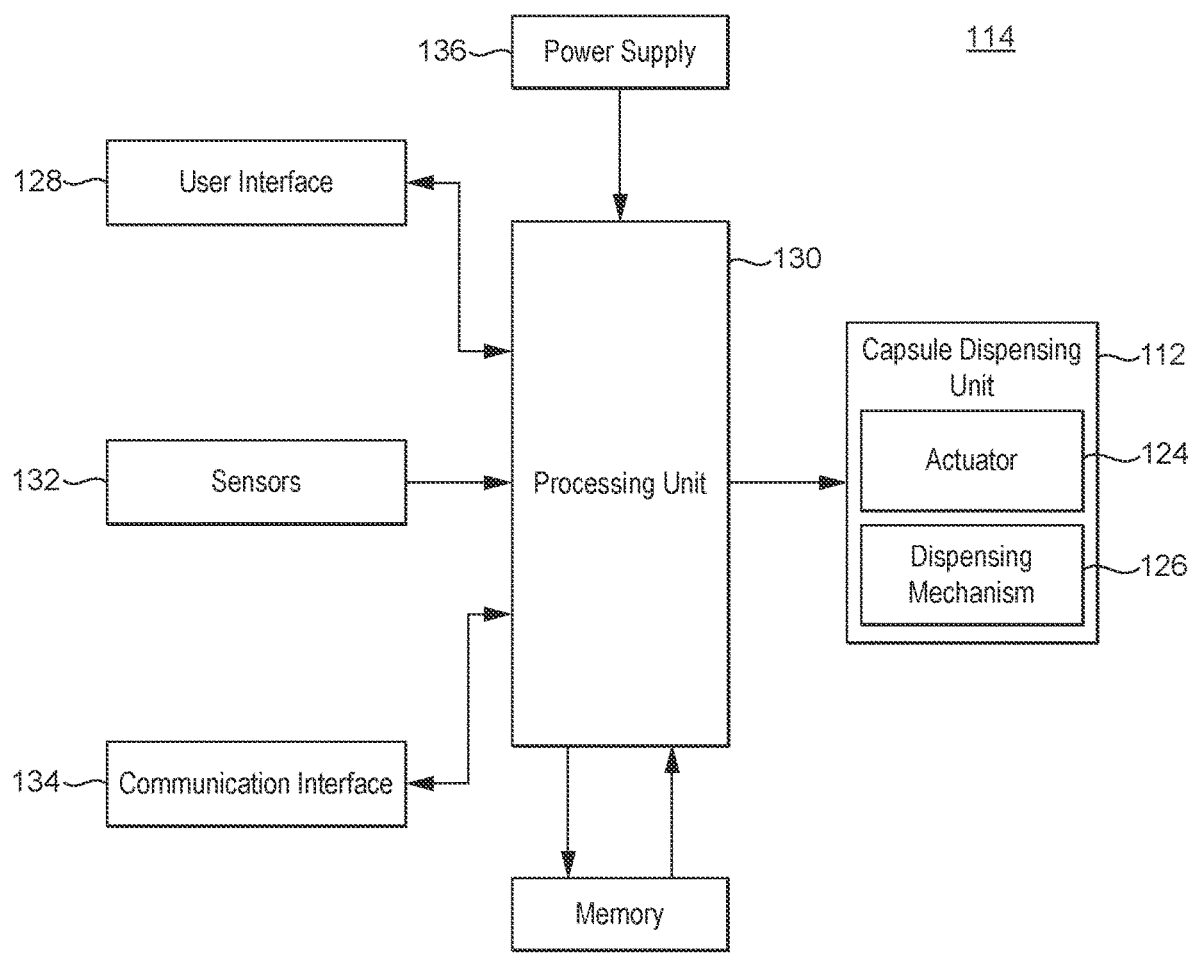
FIG. 8 is a schematic diagram of a control system of the capsule dispenser according to FIGS. 6 and 7.

With reference to FIG. 8, the control system 114 will now be considered: the control system 114 is operable: to receive a command from a user instructing the dispensing of a capsule 6; in response control the capsule dispensing mechanism 112; exchange data with the control system 118 of the beverage preparation machine 4. The control system 114 typically comprises at a second level of the capsule dispenser 106: a user interface 128; a processing unit 130; sensors 132; optionally a communication interface 134; a power supply 136 which are sequentially described.

The user interface 128 comprises hardware to enable a user to interface with the processing unit 132, by means of a user interface signal. More particularly: the user interface 128 receives commands from a user; the user interface signal transfers the said commands to the processing unit 132 as an input. The commands are typically to dispense a particular capsule 6 and/or to power on or off the capsule dispenser 106. The processing unit 132 may also output feedback to the user interface 128 as part of a capsule dispensing operation, e.g. to indicate that a capsule 6 has been selected.

The hardware of the user interface 128 may comprise any suitable device(s), for example, the hardware comprises one or more of the following: buttons, such as a joystick button or press button; joystick; LEDs; graphic or character LDCs; graphical screen with touch sensing and/or screen edge buttons. The user interface 128 can be formed as one unit or a plurality of discrete units. For more complicated hardware configurations the user interface 128 can comprise a separate processing unit (examples of which are provided following) to interface with the maser processing unit 130.

The user interface 128 may further comprise an identification system, which is operable to authenticate an identity of a user. The identification system may comprise: a card reader e.g. a magnetic strip reader; a key pad for entering a code; other suitable system. Using the identification system a user can be identified, e.g.: so that a dispensed capsule 6 is purchased by a user using credit associated therewith; a particular type of options are enabled for the user, such as particular capsule types, or administrator options for service of the capsule dispenser 106 and/or the beverage preparation machine 4.

The sensors 132 are operable to provide an input signal to the processing unit 130 for monitoring of the capsule dispensing operation. The input signal can be an analogue or digital signal. The sensors 132 typically comprise one or more of the following: capsule sensors operable to sense if a capsule has been dispensed; position sensors operable to sense a position of the dispensing mechanism 126 and/or actuator 124.

The processing unit 130 is operable to: receive an input, i.e. the commands from the user interface 128 and/or the signal of the sensors 132; process the input according to program code (or programmed logic) stored on a memory unit (discussed later on); provide an output, which is generally an the dispensing of a capsule 6 via the capsule dispensing system 112 and associate data exchange with the processing unit 56 of the beverage preparation machine 4 via the communication interface 134. More specifically, the output comprises the operation of: operation of the actuator 124 of the capsule dispensing system 112 to dispense a capsule. Operation of the aforesaid can be open-loop control, or more preferable (in certain non-limiting embodiments) closed-loop control using the input signal from the sensors 132 as feedback.

The processing unit 130 may comprise an integrated circuit such as one of the examples previously described for the processing unit 58 of the beverage preparation machine 4. In an alternative embodiment the processing unit 128 of the capsule dispenser 106 is integrated with that of the beverage preparation machine 4, e.g. the user interface 128, capsule dispensing system 112 and sensors 132 are connected to the processing unit 58 of the beverage preparation machine 4 or the converse, as will be discussed.

The communication interface 134 is for data communication of the capsule dispenser 106 with the beverage preparation machine 4. The communication interface 134 can be used to supply and/or receive information related to the beverage preparation operation/capsule dispensing operation as will be discussed. The communication interface 134 can be configured for cabled media or wireless media or a combination thereof as discussed previously for the communication interface 104 of the beverage preparation machine.

The power supply 136 is operable to supply electrical energy to the said controlled components, processing unit 130 and components associated therewith. The power supply 136 may comprise equivalent means to the power supply 102 of the beverage preparation machine 4 or share the said power supply.

Interoperability of Beverage Preparation Machine and Capsule Dispenser

A control system of the beverage preparation system 2 is configured to: determine a running count of the number of capsule dispensing operations; determine a running count of the number of beverage preparation operations; determine therefrom the inter-operability of the beverage preparation machine 4 and capsule dispenser 106, which will be discussed.

The said control system may be formed by various arrangements e.g.: the control system is formed in part from the control system 18 of the beverage preparation machine and the control system 114 of the capsule dispenser and a separate further processing unit that interfaces via the communication interfaces 104, 134 with the processing units 58, 130; the control system comprises the processing unit 58 or 130 of one of the capsule dispenser 106 or the beverage preparation machine 4 that interfaces over a communication interface directly with the components of the other of the capsule dispenser 106 or the beverage preparation machine 4, i.e. a single processing unit is used to control both the capsule dispenser 106 or the beverage preparation machine 4; in a particular (but non-limiting) example the control system comprises the control system 18 of the beverage preparation machine 4 and the control system 114 of the capsule dispenser 106, whereby the associated processing units interface via the communication interfaces 104, 134.

The said counts may be performed by the processing unit of either the beverage preparation machine 4 or the capsule dispenser 106 (or the said optional other processing unit) or a combination thereof with data in relation to the relevant process being exchanged over the relevant communication interface, e.g.: the processing unit 56 of the beverage preparation machine 4 determines a running count of the number of beverage preparation operations and stores it on its non-volatile and/or volatile memory and the processing unit 130 of the capsule dispenser 106 determines a running count of the number of capsule dispensing operations and stores to on its non-volatile and/or volatile memory; one of the beverage preparation machine 4 or the capsule dispenser 106 communicates data relating to the associated process to the other of the beverage preparation machine 4 or the capsule dispenser 106 which performs both counts.

In a particular (but non-limiting) example, the processing unit 130 of the capsule dispenser 106 determines the running count of the number of capsule dispensing operations and receives a signal from the beverage preparation machine 4 over the communication interface 104, 134 relating to the beverage preparation operation from which the capsule dispenser 106 determines the running count of the number of beverage preparation operations. The processing unit 130 of the capsule dispenser 106 can process the running counts and in response enable/disable capsule dispensing, and send a signal to the beverage preparation machine 4 over the communication interface 104, 134 to enable/disable its operation.

With such an example, the processing unit 58 of the beverage preparation machine 4 can be set to default operation of the machine to a state wherein the beverage preparation operation is disabled and enable the said process upon receiving a signal over the communication interface from the processing unit 130 of the capsule dispenser 106. Advantageously, if communication between the capsule dispenser 106 and beverage preparation machine 4 is disrupted, e.g. in the example of a cable connection a user cuts the cable, then the beverage preparation operation is prevented. In addition, the processing units of the capsule dispenser 106 and the beverage preparation machine 4 may be configured such that nether devices operate unless they are in communication with each other.

The program code (and/or programmed logic) of the relevant processing unit is configured when executed to compare the a running count of the number of capsule dispensing operations (termed hereon as the dispensing count) to the running count of the number of beverage preparation operations (termed hereon as the beverage preparation count) and in response enable/disable operation of the beverage preparation machine 4 and/or enable/disable operation of the capsule dispenser 106, examples of which will now be provided:

The operation of the beverage preparation system 2 can be controlled such that the use of capsules 6, which have not been dispensed from the capsule dispenser 106, is restricted in the beverage preparation machine 4 by one of the following conditions:

Disable the beverage preparation operation (e.g. it is switched from enabled to disabled or maintained as disabled) IF dispensing count is less than or equal to beverage preparation count. Disable the beverage preparation operation (e.g. it is switched from enabled to disabled or maintained as disabled) IF dispensing count is less than the beverage preparation count by more than first predetermined amount (the latter condition may be equivalently expressed as disable the beverage preparation operation IF beverage preparation count minus the dispensing count is greater than the first predetermined value). Generally the above first and second logic conditions are not implemented on the same system i.e. they are mutually exclusive and are alternative options.

The first of the conditions can be illustrated with the following two examples:

E.g. 0 capsules are dispensed so the dispensing count is 0; 0 beverages are prepared so the beverage preparation count is 0; the dispensing count is equal to the beverage preparation count so the beverage preparation machine 4 is disabled. Such a condition generally occurs on start-up of the system 2 (or after counter re-set as will be discussed)

E.g. 0 capsules are dispensed so the dispensing count is 0; 2 beverages are prepared so the beverage preparation count is 2; the dispensing count is less than the beverage preparation count so the beverage preparation machine 4 is disabled. In general such a condition would not occur during normal operation of the system 2 since during execution of the associated logic loop (an example of which is shown later on) the previous condition would prevent the occurrence of this condition.

The second of the conditions can be illustrated with the following example:

E.g. 0 capsules are dispensed so the dispensing count is 0; 2 beverages are prepared so the beverage preparation count is 2; the first predetermined amount is set to 1; the dispensing count is less than the beverage preparation count by more than the first predetermined amount so the beverage preparation machine 4 is disabled. Such a condition is useful in enabling a limited amount (i.e. the first predetermined amount) of capsules which have not been dispensed from the capsule dispenser 106 to be used on the beverage preparation machine 4. It also enables a limited amount of capsules that have been dispensed by the capsule dispenser 106 to be used on the beverage preparation machine 4 after a condition comprising a counter reset following a lapse of a predetermined amount of time, as will be discussed.

Conversely, the beverage preparation operation can be enabled (e.g. it is switched from disabled to enabled or maintained as enabled) IF the dispensing count is greater than the beverage preparation count or IF the dispensing count is less than the beverage preparation count by less than or equal to the first predetermined amount.

E.g. 2 capsules are dispensed so the dispensing count is 2; 0 beverages are prepared so the beverage preparation count is 0; the dispensing count is greater than the beverage preparation count so the beverage preparation machine 4 is enabled.

E.g. 0 capsules are dispensed so the dispensing count is 0; 2 beverages are prepared so the beverage preparation count is 2; the first predetermined amount is set to 2; the dispensing count is less than the beverage preparation count by the first predetermined amount so the beverage preparation machine 4 is enabled. In this way the beverage preparation system 2 can control the extraction of a limited amount (i.e. the first predetermined amount) of capsules that were not dispensed from the capsule dispenser 106.

E.g. 0 capsules are dispensed so the dispensing count is 0; 1 beverage is prepared so the beverage preparation count is 1; the first predetermined amount is set to 2; the dispensing count is less than the beverage preparation count by less than first predetermined amount so the beverage preparation machine 4 is enabled. In this way the beverage preparation system 2 can control the extraction of a limited amount (i.e. the first predetermined amount) of capsules that were not dispensed from the capsule dispenser 106.

The condition of A) above is advantageous if for example a proprietor/leaser of the beverage preparation system 2 uses capsule 6 sales to fund the purchase lease of the beverage preparation system 2.

The operation of the beverage preparation system 2 can be controlled such that the dispensing of capsules 6 from the capsule dispenser 106 for use in beverage preparation machines other than the beverage preparation machine 4 is restricted by the following condition:

Disable the capsule dispensing operation (e.g. it is switched from enabled to disabled or maintained as disabled) IF dispensing count is greater than or equal to the beverage preparation count by a second predetermined amount (the aforesaid condition can be alternatively phrased as disable a subsequent capsule dispensing operation if the dispensing count is greater than or equal to the sum of the beverage preparation count and a second predetermined amount).

E.g. 10 capsules are dispensed so the dispensing count is 10; 0 beverages are prepared so the beverage preparation count is 0; the second predetermined amount is 10; the dispensing count is equal to the beverage preparation count plus the second predetermined amount so the capsule dispenser 106 is disabled.

E.g. 15 capsules are dispensed so the dispensing count is 15; 0 beverages are prepared so the beverage preparation count is 0; the second predetermined amount is 10; the dispensing count is greater than the beverage preparation count plus the second predetermined amount so the capsule dispenser 106 is disabled. In general such a condition would not occur during normal operation of the system 2 since during execution of the associated logic loop (an example of which is shown later on) the previous condition would prevent the occurrence of this condition.

Conversely, the capsule dispensing operation can be enabled (e.g. it is switched from disabled to enabled or maintained as enabled) IF dispensing count is greater than the beverage preparation count by less than the second predetermined amount.

E.g. 5 capsules are dispensed so the dispensing count is 5; 0 beverages are prepared so the beverage preparation count is 0; the second predetermined amount is 10; the dispensing count is greater than the beverage preparation count by less than second predetermined amount so the capsule dispenser 106 is enabled.

In response to the aforesaid inequality, a subsequent beverage preparation operation may be enabled or disabled, e.g. a subsequent beverage preparation operation is disabled IF dispensing count is greater than or equal to the sum of the beverage preparation count and a second predetermined amount. In this way the beverage preparation machine is permanently disabled in the event of excessive accumulation of capsules, and may for example require re-setting by an administrator.

The condition of B) is advantageous if for example a proprietor/leaser of the beverage preparation system 2 discounts the capsules 6 dispensed therefrom for use in their establishment and wishes to restrict users purchasing the discounted capsules to be used elsewhere/stockpiled, e.g. a particular user purchases all the remaining stock of a particular capsule type.

The second predetermined amount is advantageous in setting the amount of capsules that can be dispensed (and thus the number of capsules potentially stockpiled) above dispensing operations before the capsule dispenser is locked. The first predetermined amount is typically a number greater than zero, e.g. any number between 1-50, typically it is a number greater than or equal to 5 or 10 or 15. Generally condition B) is executed within a logic loop which includes condition A) executed first as shown for the logic loop later on.

The combination of conditions A) and B) is therefore advantageous since both of the associated aspects can be restricted. An example of how conditions A) and B) can be suitably combined is shown following in program code, which comprises a logic loop (note as indicated by an (or), for condition A) both alternative logic conditions are shown however generally only one of these alternatives is implemented).

IF dispensing count LE beverage preparation count (or) IF dispensing count+first predetermined amount LT beverage preparation count THEN disable beverage preparation operation IF dispensing count GT beverage preparation count (or) IF dispensing count+first predetermined amount GE beverage preparation count THEN enable beverage preparation operation IF dispensing count GE beverage preparation count+second predetermined amount THEN disable capsule dispensing operation IF dispensing count LT beverage preparation count+second predetermined amount THEN enable capsule dispensing operation

ENDIF

For each increment of either the dispensing count or the beverage preparation count the above logic loop can be executed.

The program code (and/or programmed logic) may be configured to adjust, e.g. reset, the beverage preparation count and/or the dispensing count following a predetermined amount of time of inactivity of either or both of the counts, examples of which are provided. The predetermined amount of time can be determined by a clock generator of/or associated with the processing unit.

Following the dispensing of a capsule 6 from the capsule dispenser 106 (and the corresponding incrementing of the dispensing counter), IF a beverage preparation operation is not executed in a predetermined amount of time from the dispensing process (and the corresponding beverage preparation count incremented) THEN the dispensing count and optionally the beverage preparation count can be reset. The predetermined amount of time can be a user defined amount, e.g. 5, 10, 20 minutes.

This functionality is advantageous since the user can be given a reasonable amount of time to use a dispensed capsule 6 in the beverage preparation machine 4 following dispensing. As an example, in a busy establishment and/or with a beverage preparation system 2 configuration wherein the capsule dispenser 106 is separate from the beverage preparation machine 4: the predetermined amount of time can be set by the proprietor/leaser of the machine to be a longer period of time, such as 10-20 minutes, to account for queues at the beverage preparation machine 4.

The above logic loop can be modified to include an initial step of the said reset operation by the further portion of program code:

IF dispensing count GT 0 AND beverage preparation operation not executed on beverage preparation machine 4 within predetermined time from last dispensing process THEN dispensing count=0

It is to be appreciated that there are various mathematically equivalent methods for achieving the above conditions of A, B and C. For example, a system count may be incremented for each dispensing operation and decremented for each beverage preparation operation or the converse, with the system count being compared against a value to determine the aforesaid conditions.

In an example wherein the system count is incremented by a predetermined amount such as 1 for each dispensing operation and decremented by the predetermined amount for each beverage preparation, mathematically equivalent conditions A, B and C are determined as follows:

For condition for A), the beverage preparation operation can be disabled IF system count is less than or equal to 0 or less than 0 by more than the first predetermined amount.

Conversely the beverage preparation operation can be enabled IF system count is greater than 0 or less than 0 by less than or equal to the first predetermined amount.

For condition for B), the capsule dispensing operation can be disabled IF system count is greater than or equal to the second predetermined amount.

Conversely the dispensing operation can be enabled IF system count is less than the second predetermined amount.

For condition C) the system count can be reset IF following a predetermined amount of time the system count is not decremented.

Beverage Preparation System

The beverage preparation system 2 may comprise a single capsule dispenser 106 and a single beverage preparation machine 4 which are operatively linked to operate with the aforesaid functionality.

The beverage preparation system 2 may comprise a single capsule dispenser 106 and a plurality of beverage preparation machines 4 which are operatively linked to operate with the aforesaid functionality. In FIG. 6 an example is provided wherein the capsule dispenser 106 is operatively linked to a first 4A and second 4B beverage preparation machine. With such an example the control system is configured to receive beverage preparation information from each of the beverage preparation machines, and to determine therefrom an aggregate beverage preparation count comprising a single running count of the beverage preparation operations for the plurality of beverage preparation machines. The aggregate counts are used when determining whether the aforesaid conditions occur (e.g. operations A) and B) and the predetermined amount of time). With such an example, the above logic to disable the beverage preparation machine results in the disabling of all operatively linked beverage preparation machines. Moreover when the control system is configured to reset a count after a predetermined amount of time the control system can be configured to set the dispensing count and/or the aggregate beverage preparation count to the said predetermined amount (typically 0) if for all of the said beverage preparation machines the predetermined amount of time lapses following a dispensing operation without a beverage preparation operation, i.e. if on a single beverage preparation machine 4 a beverage is prepared within the predetermined amount of time then the counter is not reset.

The beverage preparation system 2 may further comprise a plurality of capsule dispensers 106 and one or a plurality of beverage preparation machines 4 which are operatively linked to operate with the aforesaid functionality. With such an example the control system is configured to receive beverage preparation information from each of the beverage preparation machines, and to determine therefrom an aggregate beverage preparation count comprising a single running count of the beverage preparation operations for the plurality of beverage preparation machines. Likewise, with such an example the control system is configured to receive capsule dispensing information from each of the capsule dispensers, and to determine therefrom an aggregate dispensing count comprising a single running count of the capsule dispensing operations for the plurality of beverage preparation machines. The aggregate counts are used when determining whether the aforesaid conditions occur (e.g. operations A) and B) and the predetermined amount of time). With such an example, the above logic to: disable the beverage preparation machine results in the disabling of all operatively linked beverage preparation machines; disable the capsule dispenser results in the disabling of all operatively linked capsule dispensers. Counter re-set is controlled as for the aforesaid example.

LIST OF REFERENCES

2 Beverage Preparation System
4 Beverage Preparation Machine
   10 Housing
      20 Base
      22 Body
   12 Fluid supply
      24 Reservoir
      26 Fluid pump
      28 Fluid heater
   14 Extraction unit
      30 Injection head
         40 Injector
      32 Capsule holder
         42 Cavity
            44 Cavity Base
         46 Extraction wall
            48 Outlet
      34 Capsule holder loading mechanism
      36 Capsule insertion channel
      38 Capsule Ejection channel
   16 Capsule processing unit
      50 Code reading system
         74 Code reader
         Code reading mechanism 52 Capsule transfer mechanism
   Movable capsule support
   Actuator
54 Capsule detection system
   Capsule detection sensors
18 Control system
  56 User interface
  58 Processing unit
    62 Memory
      Programs or programmed logic
  60 Sensors
    62 Fluid level sensors
    64 Flow rate sensors
    66 Temperature sensors
    68 Position sensors
    70 Fluid level sensors
    72 Capsule detection sensors
    74 Code reader
    76 Capsule support
    80 Angular velocity sensors
  102 Power Supply
  104 Communication interface
6 Capsule
100 Capsule axis of rotation
Example 1
82 Body portion
84 Lid portion
86 Flange portion
Example 2
88 Body portion
90 Lid portion
92 Flange portion
Example 3
94 Body portion
96 Lid portion
98 Flange portion
8 Receptacle
106 Capsule Dispenser
  108 Housing
    116 Base
    118 Body
  110 Capsule holder
    120 Body
    122 Cartridge
  112 Capsule Dispensing system
    124 Actuator
    126 Dispensing mechanism
  114 Control system
    128 User interface
    130 Processing unit
    132 Sensors
    134 Communication interface
    136 Power supply

The invention claimed is:

1. A beverage preparation system comprising:
a capsule dispenser to dispense a capsule to a user as a capsule dispensing operation;
a beverage preparation machine to extract an ingredient of a beverage from the capsule supplied thereto by the user as a beverage preparation operation, the capsule dispenser and the beverage preparation machine being operatively linked by a control system, the control system comprises a first control device, the first control device is associated with the beverage preparation machine and comprises (i) a first processing unit, (ii) a first user interface configured to transfer an instruction from the user to the first processing unit to execute an extraction process, adjust an operational parameter of the beverage preparation machine, and/or to power on or off the beverage preparation machine, and (iii) a first sensor configured to provide a signal to the first processing unit regarding the extraction process and/or a status of the beverage preparation machine; the control system further comprises a second control device, the second control device is associated with the capsule dispenser and comprises (a) a second processing unit separate from the first processing unit, (b) a second user interface configured to transfer an instruction from the user to the second processing unit to dispense a particular capsule and/or to power on or off the capsule dispenser, and (c) a second sensor configured to provide a signal to the second processing unit regarding the capsule dispensing operation;
the control system being configured to:
obtain dispensing information for determining a dispensing count, which comprises a running count of capsule dispensing operations;
obtain beverage preparation information for determining a beverage preparation count, which comprises a running count of beverage preparation operations; and
wherein the control system is configured to disable a subsequent beverage preparation operation if the dispensing count is less than or equal to the beverage preparation count or if the dispensing count is less than the beverage preparation count by more than a first predetermined amount.

2. The beverage preparation system according to claim 1, wherein the control system is configured to enable the subsequent beverage preparation operation if the dispensing count is greater than the beverage preparation count or if the dispensing count is less than the beverage preparation count by less than or equal to the first predetermined amount.

3. The beverage preparation system according to claim 1, wherein the control system is configured to enable the subsequent capsule dispensing operation if the dispensing count is less than or equal to the beverage preparation count or if the dispensing count is less than the beverage preparation count by more than the first predetermined amount.

4. The beverage preparation system according to claim 1, wherein the control system is configured to disable the subsequent capsule dispensing operation if the dispensing count is greater than or equal to a sum of the beverage preparation count and a second predetermined amount.

5. The beverage preparation system according to claim 4, wherein the control system is configured to enable the subsequent capsule dispensing operation if the dispensing count is less than the sum of the beverage preparation count and the second predetermined amount.

6. The beverage preparation system according to claim 4, wherein the control system is configured to disable the subsequent beverage preparation operation if the dispensing count is greater than or equal to the sum of the beverage preparation count and the second predetermined amount.

7. The beverage preparation system according to claim 1, wherein the control system is configured to set at least one of the dispensing count and the beverage preparation count to a predetermined amount if a predetermined amount of time lapses following a dispensing operation without the beverage preparation operation.

8. The beverage preparation system according to claim 1, wherein the beverage preparation machine and the capsule dispenser are operatively linked via the control system by cabled or wireless media and the control system is configured to disable the beverage preparation machine or the capsule dispenser if the other of the beverage preparation machine or the capsule dispenser is operatively disconnected from the control system.

9. The beverage preparation system according to claim 1, comprising a plurality of beverage preparation machines, which are operatively connected to the control system, the control system configured to receive beverage preparation information from each of the plurality of beverage preparation machines, for determining therefrom the beverage preparation count comprising a running count of the beverage preparation operations for the plurality of beverage preparation machines.

10. The beverage preparation system according to claim 7, comprising a plurality of beverage preparation machines which are operatively connected to the control system, the control system configured to receive beverage preparation information from each of the plurality of beverage preparation machines, for determining therefrom the beverage preparation count comprising a running count of the beverage preparation operations for the plurality of beverage preparation machines, and wherein the control system is configured to set at least one of the dispensing count and the beverage preparation count or an equivalent count that can be derived therefrom to the predetermined amount if for all of the plurality of beverage preparation machines the predetermined amount of time lapses following the dispensing operation without the beverage preparation operation.

11. A capsule dispenser to dispense a capsule to a user as a capsule dispensing operation, the capsule dispenser comprising a control system to:
obtain dispensing information for determining a dispensing count, which comprises a running count of capsule dispensing operations;
obtain beverage preparation information for determining a beverage preparation count or obtain the beverage preparation count, which comprises a running count of beverage preparation operations;
wherein the control system is configured to effect the disabling of a subsequent beverage preparation operation if the dispensing count is less than or equal to the beverage preparation count or if the dispensing count is less than the beverage preparation count by more than a first predetermined amount; and
wherein the control system comprises a first control device, the first control device is associated with the beverage preparation machine and comprises (i) a first processing unit, (ii) a first user interface configured to transfer an instruction from the user to the first processing unit to execute an extraction process, adjust an operational parameter of the beverage preparation machine, and/or to power on or off the beverage preparation machine, and (iii) a first sensor configured to provide a signal to the first processing unit regarding the extraction process and/or a status of the beverage preparation machine; the control system further comprises a second control device, the second control device is associated with the capsule dispenser and comprises (a) a second processing unit separate from the first processing unit, (b) a second user interface configured to transfer an instruction from the user to the second processing unit to dispense a particular capsule and/or to power on or off the capsule dispenser, and (c) a second sensor configured to provide a signal to the second processing unit regarding the capsule dispensing operation.

12. A beverage preparation machine to extract an ingredient of a beverage from a capsule supplied thereto by a user as a beverage preparation operation, the beverage preparation machine comprising a control system configured to:
obtain dispensing information for determining a dispensing count or obtain the dispensing count, which comprises a running count of capsule dispensing operations;
obtain beverage preparation information for determining a beverage preparation count, which comprises a running count of beverage preparation operations;
wherein the control system is configured to effect the disabling of a subsequent beverage preparation operation if the dispensing count is less than or equal to the beverage preparation count or if the dispensing count is less than the beverage preparation count by more than a first predetermined amount; and
wherein the control system comprises a first control device, the first control device is associated with the beverage preparation machine and comprises (i) a first processing unit, (ii) a first user interface configured to transfer an instruction from the user to the first processing unit to execute an extraction process, adjust an operational parameter of the beverage preparation machine, and/or to power on or off the beverage preparation machine, and (iii) a first sensor configured to provide a signal to the first processing unit regarding the extraction process and/or a status of the beverage preparation machine; the control system further comprises a second control device, the second control device is associated with the capsule dispenser and comprises (a) a second processing unit separate from the first processing unit, (b) a second user interface configured to transfer an instruction from the user to the second processing unit to dispense a particular capsule and/or to power on or off the capsule dispenser, and (c) a second sensor configured to provide a signal to the second processing unit regarding the capsule dispensing operations.

* * * * *